(12) United States Patent
Efrat

(10) Patent No.: US 8,039,254 B2
(45) Date of Patent: Oct. 18, 2011

(54) POPULATIONS OF EXPANDED AND RE-DIFFERENTIATED ADULT ISLET BETA CELLS CAPABLE OF PRODUCING INSULIN AND METHODS OF GENERATING SAME

(75) Inventor: Shimon Efrat, Zikhron-Yaakov (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 177 days.

(21) Appl. No.: 11/791,170

(22) PCT Filed: Nov. 21, 2005

(86) PCT No.: PCT/IL2005/001231
§ 371 (c)(1),
(2), (4) Date: May 21, 2007

(87) PCT Pub. No.: WO2006/054305
PCT Pub. Date: May 26, 2006

(65) Prior Publication Data
US 2008/0014182 A1    Jan. 17, 2008

Related U.S. Application Data

(60) Provisional application No. 60/629,351, filed on Nov. 22, 2004.

(51) Int. Cl.
*C12N 5/07* (2010.01)
(52) U.S. Cl. .................................. 435/325; 435/377
(58) Field of Classification Search .................. 435/325, 435/377
See application file for complete search history.

(56) References Cited

U.S. PATENT DOCUMENTS

| | | | |
|---|---|---|---|
| 5,681,587 A * | 10/1997 | Halberstadt et al. ........... | 424/562 |
| 2002/0155598 A1 * | 10/2002 | Kerr-Conte et al. ........... | 435/325 |
| 2003/0072754 A1 * | 4/2003 | Kenyon et al. .............. | 424/144.1 |
| 2003/0175963 A1 * | 9/2003 | Rosenberg .................... | 435/375 |
| 2004/0132183 A1 * | 7/2004 | Scharp et al. ................. | 435/366 |
| 2004/0132679 A1 | 7/2004 | Chan et al. | |

FOREIGN PATENT DOCUMENTS

| WO | WO 00/78929 | 12/2000 |
|---|---|---|
| WO | WO 03/100026 | 4/2003 |
| WO | WO 2005/026335 | 3/2005 |

OTHER PUBLICATIONS

Maria-Engler et al. 2004. Co-localization of nestin and insulin and expression of islet cell markers in long-term human pancreatic nestin-positive cell cultures. Journal of Endocrinology. 183, p. 455-467.*

Heremans et al. 2002. Recapitulation of embryonic neuroendocrine differentiation in adult human pancreatic duct cells expressing neurogenin 3. The Journal of Cell Biology, vol. 159, No. 2, pp. 303-311.*
Dor et al. "Adult Pancreatic β-Cells Are Formed by Self-Duplication Rather Than Stem-Cell Differentiation", Nature, 429(6987): 41-46, 2004.
Ouziel-Yahalom et al. "Expansion and Redifferentiation of Adult Human Pancreatic Islet Cells", Biochemical and Biophysical Research Communications, 341(2): 291-298, 2006.
Response Dated Feb. 22, 2010 to Communication Pursuant to Article 94(3) EPC of Nov. 2, 2009 From the European Patent Office Re.: Application No. 05808277.7.
Response Dated Feb. 22, 2010 to Communication Pursuant to Article 94(3) EPC of Nov. 2, 2009 From the European Patent Office Re.: Application No. 05808277.7.
Communication Pursuant to Article 94(3) EPC Dated Nov. 2, 2009 From the European Patent Office Re.: Application No. 05808277.7.
Communication Pursuant to Article 94(3) EPC Dated Feb. 25, 2008 From the European Patent Office Re.: Application No. 05808277.7.
International Preliminary Report on Patentability Dated May 31, 2007 From the International Bureau of WIPO Re.: Application No. PCT/IL2005/001231.
International Search Report Dated Jul. 25, 2006 From the International Searching Authority Re.: Application No. PCT/IL2005/001231.
Written Opinion Dated Jul. 25, 2006 From the International Searching Authority Re.: Application No. PCT/IL2005/001231.
Communication Pursuant to Article 94(3) EPC Dated Nov. 2, 2009 From the European Patent Office Re.: Application No. 05808277.7.
Communication Pursuant to Article 94(3) EPC Dated Feb. 25, 2008 From the European Patent Office Re.: Application No. 05808277.7.
International Preliminary Report on Patentability Dated May 31, 2007 From the International Bureau of WIPO Re.: Application No. PCT/IL2005/001231.
International Search Report Dated Jul. 25, 2006 From the International Searching Authority Re.: Application No. PCT/IL2005/001231.
Written Opinion Dated Jul. 25, 2006 From the International Searching Authority Re.: Application No. PCT/IL2005/001231.
Communication Pursuant to Article 94(3) EPC Dated Feb. 25, 2008 From the European Patent Office Re.: Application No. 05808277.7.
International Preliminary Report on Patentability Dated May 31, 2007 From the International Bureau of WIPO Re.: Application No. PCT/IL2005/001231.
International Search Report Dated Jul. 25, 2006 From the International Searching Authority Re.: Application No. PCT/IL2005/001231.
Written Opinion Dated Jul. 25, 2006 From the International Searching Authority Re.: Application No. PCT/IL2005/001231.
Translation of Notice of Reason for Rejection Dated Apr. 5, 2011 From the Japanese Patent Office Re. Application No. 2007-542508.

* cited by examiner

*Primary Examiner* — Taeyoon Kim

(57) ABSTRACT

A population of expanded adult islet beta cells is provided as well as a population of expanded and redifferentiated adult islet beta cells. Methods of generation of the populations of cells are provided.

2 Claims, 9 Drawing Sheets
(8 of 9 Drawing Sheet(s) Filed in Color)

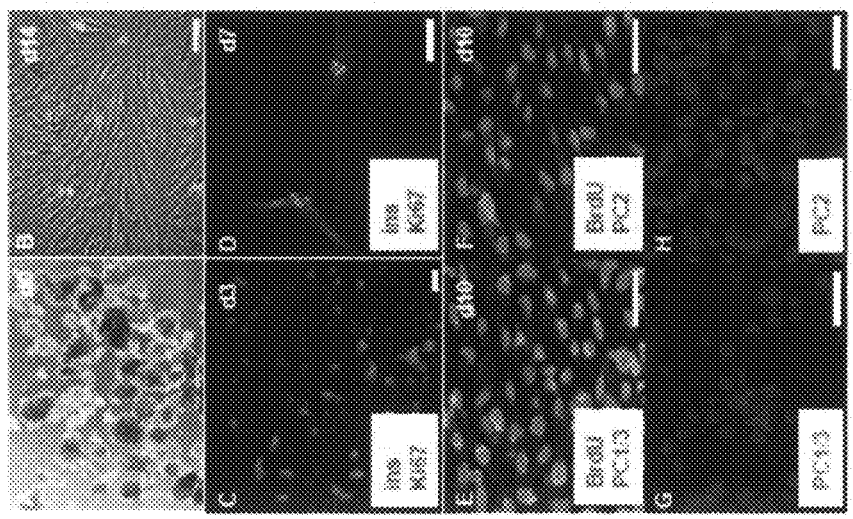
FIGs. 1A-VI

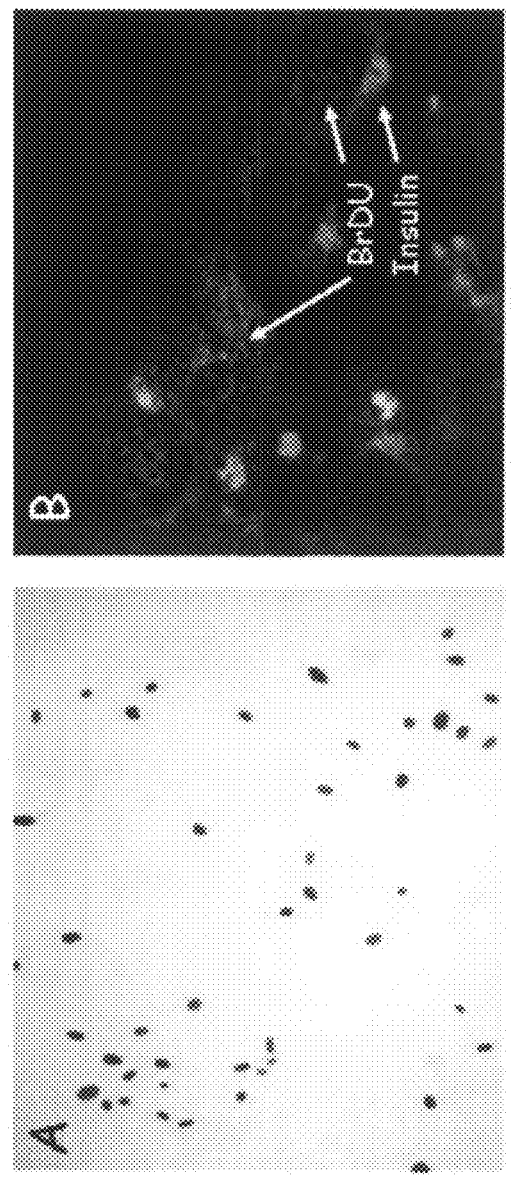
FIGs. 2A-B

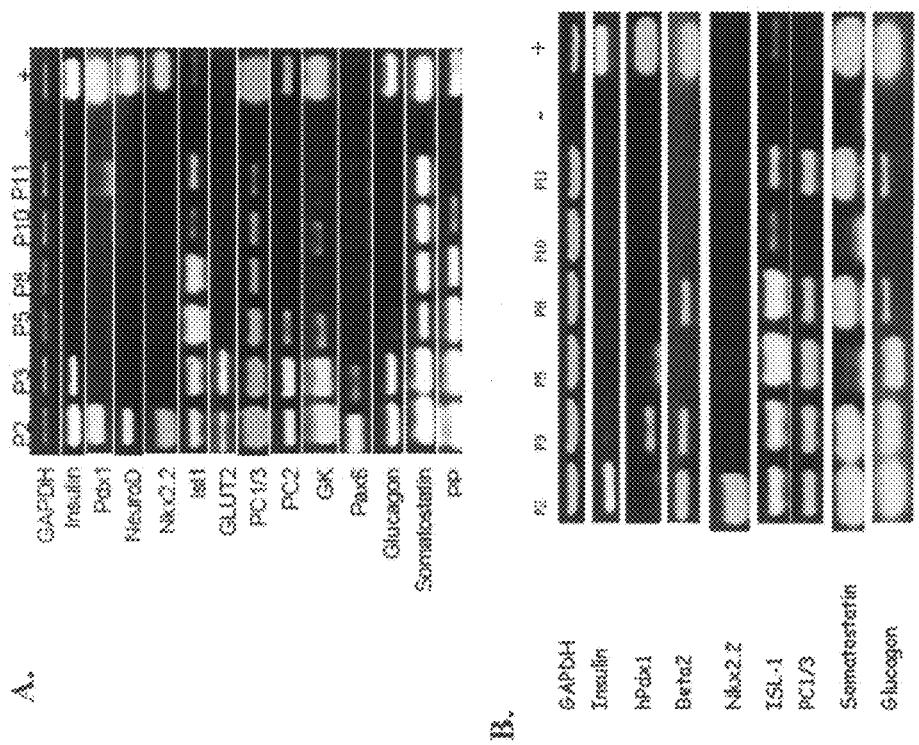

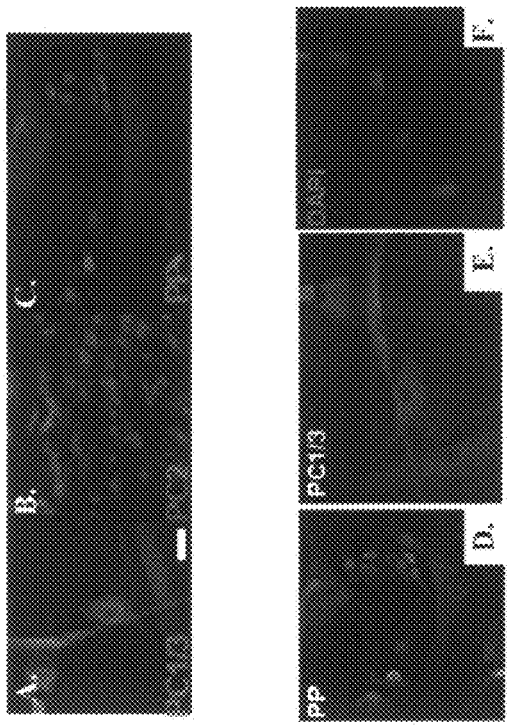
FIGs. 4A-F

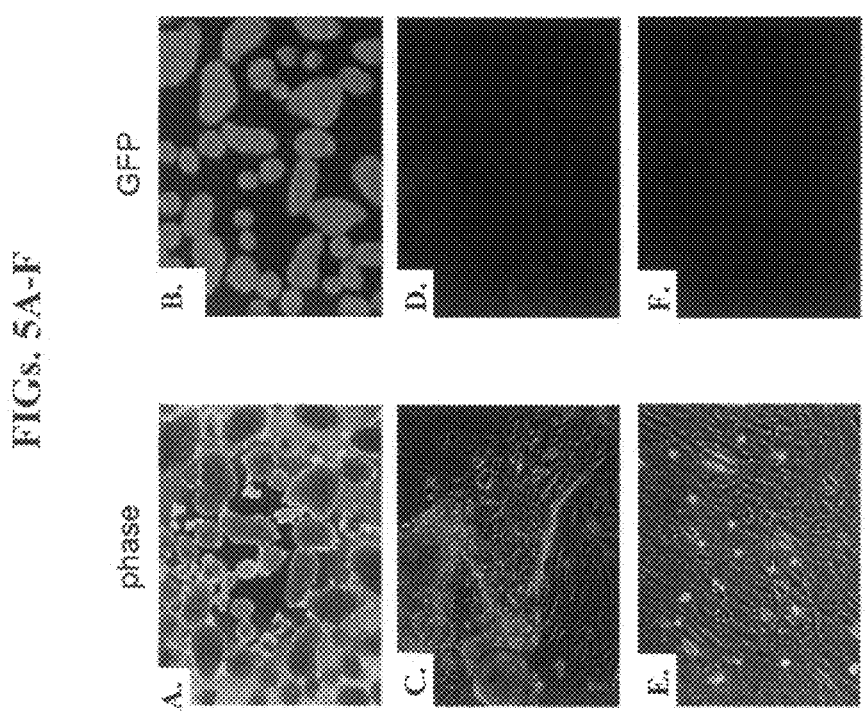
FIGS. 5A-F

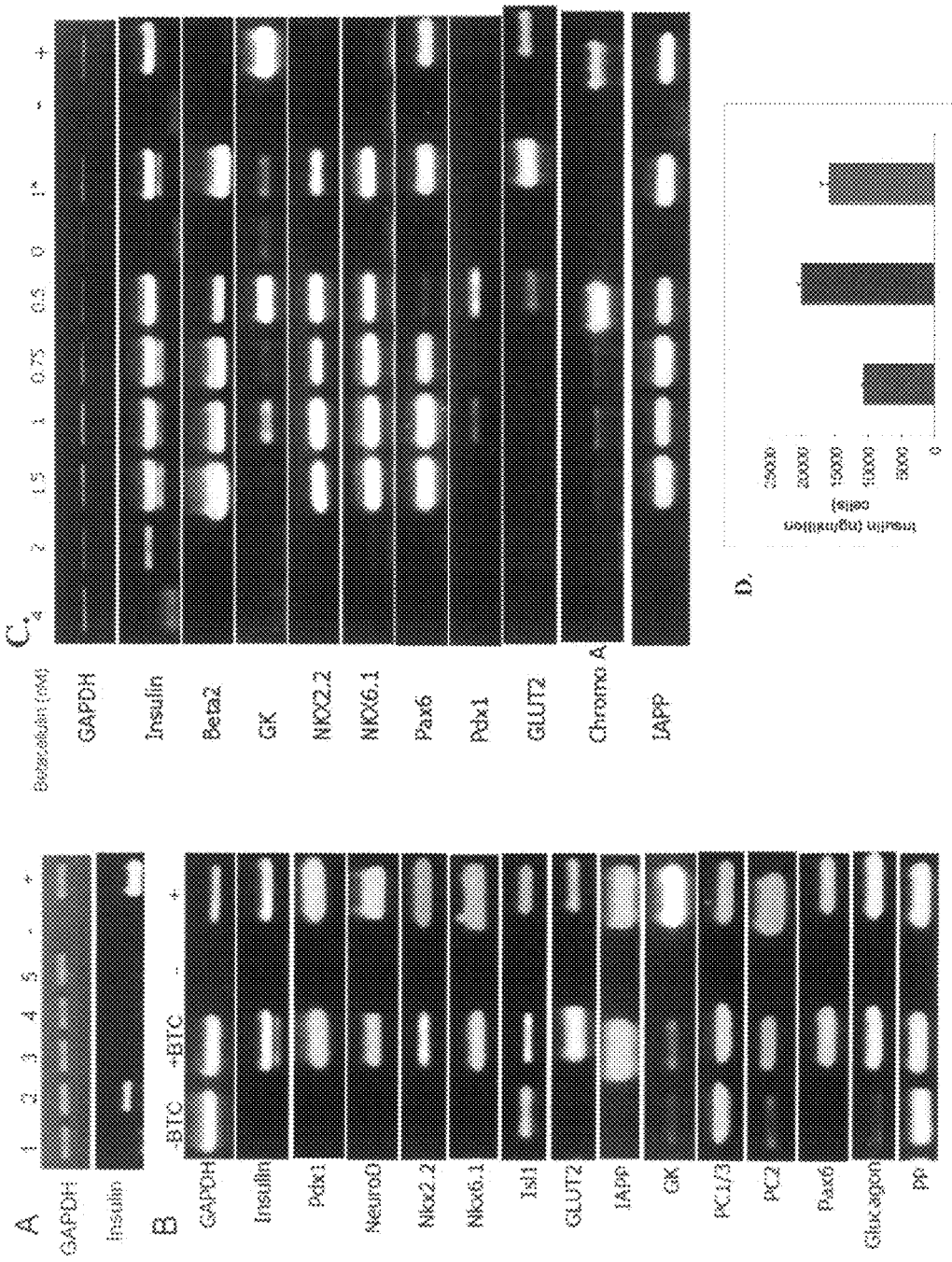
FIGS. 6A-D

FIGs. 7A-G
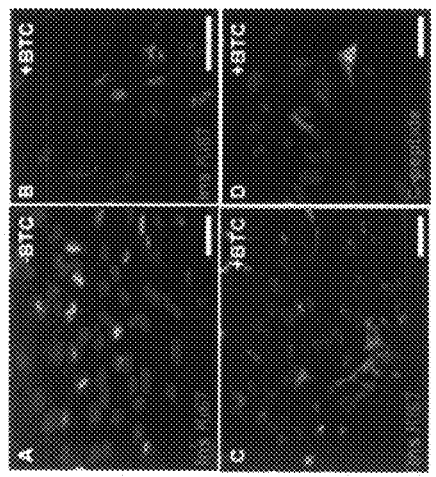
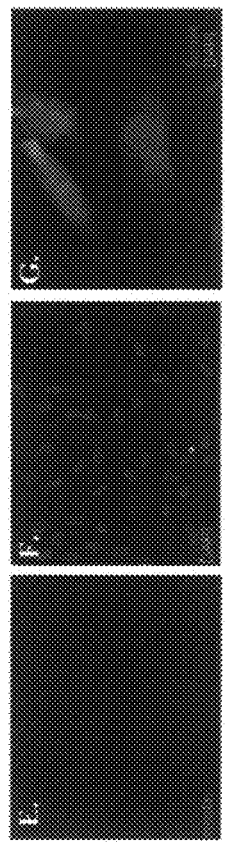

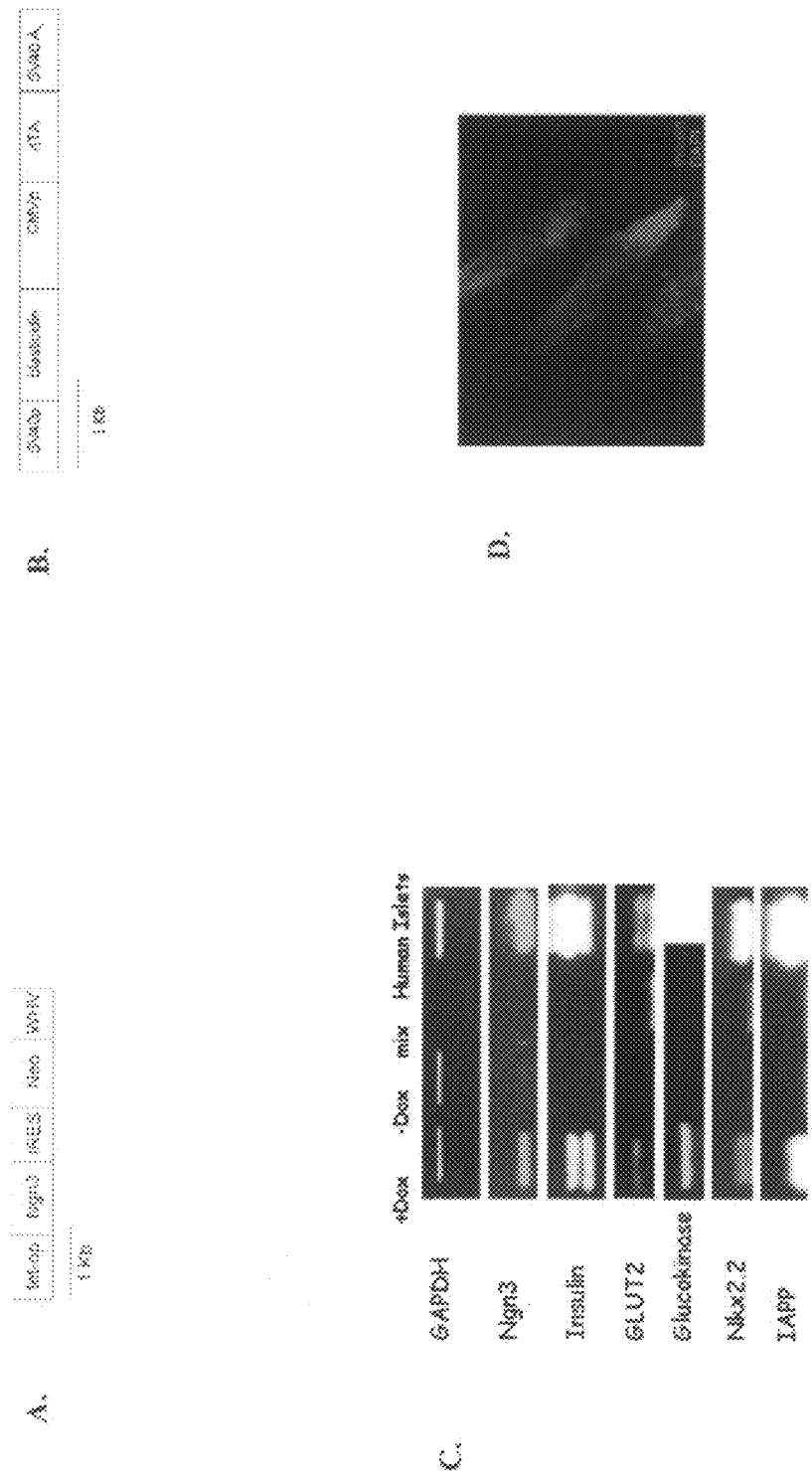
FIGs. 9A-D

```
                        SEQUENCE LISTING

<160> NUMBER OF SEQ ID NOS: 40

<210> SEQ ID NO 1
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 1
gctgcatcag aagaggcatc aggc                                          24

<210> SEQ ID NO 2
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 2
gcgtctagtt gcagtagttc tccag                                         25

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
```
accacagtcc atgccatcac     20

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
tccaccaccc tgttgctgta     20

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
aaacgctgga gcaagatgga c     21

<210> SEQ ID NO 6
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 6
gggcaggtag gagtcaggag tag     23

<210> SEQ ID NO 7
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 7
cgttcccttc aagacacaga ggag     24

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
tccctggcgg caagattatc     20

<210> SEQ ID NO 9
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 9
tcactgtggg cgtggatgg     19

<210> SEQ ID NO 10
<211> LENGTH: 22
<212> TYPE: DNA
<213> ORGANISM: Artificial sequence

```
<220> FEATURE:
<223> OTHER INFORMATION: Single strand DNA oligonucleotide

<400> SEQUENCE: 10
accgaaaaac tgagggaaga gg                                              22

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
gcacgacctc aactcggcac                                                 20

<210> SEQ ID NO 12
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 12
cctctccctt acccttagca ccc                                             23

<210> SEQ ID NO 13
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 13
aagaactaca tctgggctct gtcg                                            24

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
gctgaggggt ccatcaaagg                                                 20

<210> SEQ ID NO 15
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 15
ttgaacccag gaggcggag                                                  19

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
ctgctgctaa cacacaatga aacc                                            24
```

```
<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
tctgaacctt gggagagggc                                              20

<210> SEQ ID NO 18
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 18
ggtcattttg gcaacaatca cc                                           22

<210> SEQ ID NO 19
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 19
gaccccagac tccgtcagtt tc                                           22

<210> SEQ ID NO 20
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 20
gcctcatttc atcctgctca gc                                           22

<210> SEQ ID NO 21
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 21
cttatgtgtt tttcctctttt gctgg                                       25

<210> SEQ ID NO 22
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 22
gaaccacctg ccctttagtg taac                                         24

<210> SEQ ID NO 23
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 23
```
acacgagacc cacttttttcc g                                      21

<210> SEQ ID NO 24
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 24
tgctggactt gtgcttcttc aac                                     23

<210> SEQ ID NO 25
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 25
ggcagtgaag tagcatcaat gtcc                                    24

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
tgtttggcaa ggcaatgacc                                         20

<210> SEQ ID NO 27
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 27
ccttcctttt ctccattgag gtcc                                    24

<210> SEQ ID NO 28
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 28
aggtcgtaga gtgggctgtt gg                                      22

<210> SEQ ID NO 29
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 29
ctcctaaaag acttgcggaa tcac                                    24

<210> SEQ ID NO 30
<211> LENGTH: 25
<212> TYPE: DNA
<213> ORGANISM: Artificial sequence

```
<220> FEATURE:
<223> OTHER INFORMATION: Single strand DNA oligonucleotide

<400> SEQUENCE: 30
tccacacagg cactaagaaa gactg                                              25

<210> SEQ ID NO 31
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 31
gccaaatgga gaagagaaga aaaac                                              25

<210> SEQ ID NO 32
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 32
gttgaagtgg tgcccgagg                                                     19

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
ctgcctttcc catggatgaa                                                    20

<210> SEQ ID NO 34
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 34
cgcttcttgt cctcctcctt t                                                  21

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
aaccaacacc tgtgcggctc                                                    20

<210> SEQ ID NO 36
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 36
gggctttatt ccatctctct cgg                                                23
```

```
<210> SEQ ID NO 37
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 37
gcatcaagca cagacctaca ctcg                                           24

<210> SEQ ID NO 38
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 38
gagacacaac caccctttcat ccttc                                         25

<210> SEQ ID NO 39
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 39
caatgccaca ccagagcaga tg                                             22

<210> SEQ ID NO 40
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 40
tgggagcagg gagcaagc                                                  18
```

POPULATIONS OF EXPANDED AND RE-DIFFERENTIATED ADULT ISLET BETA CELLS CAPABLE OF PRODUCING INSULIN AND METHODS OF GENERATING SAME

RELATED APPLICATIONS

This Application is a National Phase of PCT Patent Application No. PCT/IL2005/001231 having International Filing Date of Nov. 21, 2005, which claims the benefit of U.S. Provisional Patent Application No. 60/629,351 filed on Nov. 22, 2004. The contents of the above Applications are all incorporated herein by reference.

FIELD AND BACKGROUND OF THE INVENTION

The present invention relates to a population of expanded and re-differentiated adult islet beta cells capable of both storing insulin in physiological amounts and secreting insulin in response to glucose.

Type I diabetes is caused by the autoimmune destruction of the pancreatic islet insulin-producing beta cells. Insulin administration does not prevent the long-term complications of the disease, since the optimal insulin dosage is difficult to adjust. Replacement of the damaged cells with regulated insulin-producing cells is considered the ultimate cure for type 1 diabetes. Pancreas transplantation has been successful but is severely limited by the shortage of donors. With the development of new islet isolation and immunosuppression procedures, significant success has been reported using islets from 2-3 donors per recipient (Shapiro A M, Lakey J R, Ryan E A et al. New Engl J Med 2000; 343:230-238). This progress underscores the urgent need for developing alternatives to human pancreas donors, namely abundant sources of cultured human $\beta$ cells for transplantation.

Terminally differentiated, postmitotic islet cells are difficult to expand in tissue culture. Adult and fetal human islet cells grown on HTB-9 matrix in RPMI 1640 medium containing 11 mM glucose, and supplemented with 10% FBS and hepatocyte growth factor, were shown to proliferate at the most for 10-15 population doublings, after which they underwent senescence. The replication span could not be extended by expression of the catalytic subunit of human telomerase (hTERT), which was introduced into the cells with a retrovirus (Halvorsen T L, Beattie G M, Lopez A D, Hayek A, Levine F. J Endocrinol 2000; 166:103-109). Due to massive cell death, this method resulted in a 3-4 expansion of the islet cell mass.

An alternative to forced expansion of post-mitotic $\beta$ cells is the induction of differentiation of stem/progenitor cells, which have a natural self-expansion capacity, into insulin-producing cells. The directed differentiation of embryonic stem cells has generated cells that only produce low amounts of insulin, compared to $\beta$ cells, and their potential use in transplantation has met with ethical objections, as well as concerns regarding risk of teratomas.

Adult stem cells have also been differentiated into insulin-producing cells. However, the efficiency of expansion of these cell types in tissue culture and their rate of differentiation into insulin-producing cells need to be greatly improved to allow generation of significant cell numbers for transplantation.

It has been clearly demonstrated that committed cells can be at least partly reprogrammed with dominant genes that activate a cascade of developmental events. U.S. Pat. Appl. No. 20050244966 to the present inventors teaches the reprogramming of fetal hepatic cells into beta-like insulin-producing cells by expression of dominant transcription factors, such as Pdx1, that direct the development of endocrine pancreas. The human fetal liver cells were induced to produce and store mature insulin in significant amounts, about a third of those produced by normal $\beta$ cells, release it in response to physiological glucose levels, and replace $\beta$-cell function in STZ-diabetic nonobese-diabetic severe combined immunodeficient (NOD-scid) mice. The modified cells expressed multiple $\beta$-cell genes.

Islet cells have been expanded ex vivo in the presence of epidermal growth factor and nerve growth factor. Although these cells show high insulin content, they do not secrete insulin in response to glucose (Lechner A. et al., Biochem Biophys Res Commun 327:581-588, 2005).

There is thus a widely recognized need for, and it would be highly advantageous to have, abundant sources of cultured human $\beta$ cells capable of producing physiological concentrations of insulin for transplantation devoid of the above limitations.

A number of factors have been shown to promote both $\beta$-cell proliferation and differentiation in tissue culture. Members of the growth hormone family, including placental lactogen (PL), growth hormone (GH) and prolactin (PRL), induce replication in neonatal rat islet cells. Significant mitogenic effects of hepatocyte growth factor (HGF) have been observed on human fetal and adult islets and mouse islets. In the presence of activin A or nicotinamide, HGF has been shown to stimulate $\beta$-cell differentiation in cultured fetal pancreatic islets as well as a pancreatic cell line. Glucagon-like peptide 1 (GLP-1), and its more stable analog exendin-4, have been shown to stimulate $\beta$-cell proliferation and to induce insulin gene expression in a pancreatic cell line. Members of the epidermal growth factor (EGF) family, including EGF, TGF$\alpha$ and betacellulin, have also been shown to stimulate $\beta$-cell proliferation and differentiation. Betacellulin is a potent mitogen for a number of cell types, including $\beta$ cells. It was shown to increase islet neogenesis in alloxan and STZ-treated mice, and accelerate islet-regeneration in 90%-pancreatectomized rats [Li L, et al., Endocrinology 2001; 142: 5379-5385].

In a number of rodent models, betacellulin, in combination with other factors was shown to comprise differentiation capabilities. Thus, in rodent pancreatic cell lines, betacellulin was shown both alone and in combination with other factors to induce differentiation of insulin producing cells. In addition, Pdx1 expression, combined with betacellulin treatment induced insulin expression in the mouse glucagonoma cell line alpha TC1-6, and the rat intestinal cell line IEC-6. Expression of neuroD, combined with in vivo treatment with betacellulin, induced conversion of mouse liver cells into insulin-producing cells.

Betacellulin has been shown to induce proliferation of a number of human pancreatic cell types. For example, betacellulin was shown to stimulate proliferation of adult human pancreatic duct cells [Rescan et al., Laboratory Investigation (2005) 85, 65-74].

In combination with other factors, betacellulin may also enhance differentiation into insulin-producing cells. For example, together with activin A, betacellulin induced differentiation of human fetal pancreatic cells into insulin producing cells. However, while activin A was shown to comprise the differentiating activity, betacellulin was shown to comprise a mitogenic activity only [Demeterco et al., Journal of Clinical Endocrinology and metabolism, 2000, Vol. 85, No. 10 3892-3897].

U.S. Pat. Appl. No. 20040132679 teaches the administration of betacellulin in conjunction with islet cell differentiation transcription factors for the treatment of type I Diabetes. These factors were shown to enhance the differentiation of a population of hepatic cells into insulin producing cells. However, when administered alone, betacellulin had no effect on the serum glucose of STZ induced diabetic mice, indicating that betacellulin alone was not able to differentiate the hepatic cells, but rather had a mitogenic activity thereon. Furthermore, therapeutic efficacy was shown only for the in-vivo administration of the islet cell differentiation promoting factors.

In conclusion, it has never been demonstrated that betacellulin per se has insulin producing capabilities in human pancreatic cells, only mitogenic capabilities.

It has been suggested that Neurogenin 3 (Ngn3) is a key proendocrine transcription factor. This has been demonstrated by the absence of endocrine cells in mice lacking Ngn3, by lineage tracing analyses, and by ectopic expression of Ngn3. Ngn3 is involved in the lateral specification events, which control the choice between the endocrine and exocrine cell fates by mutual signaling between neighboring cells through the Notch pathway. Terminal differentiation of β cells requires shut off of Ngn3 expression.

Identification of an insulin cell differentiating factor for an expanded culture of human beta cells would be highly advantageous for cell transplantation in the treatment of diabetes.

SUMMARY OF THE INVENTION

According to the present invention there is provided a population of ex vivo expanded adult islet beta cells being propagatable ex-vivo for at least sixteen passages while demonstrating continuous expression of islet markers.

According to another aspect of the present invention there is provided a population of ex vivo expanded and re-differentiated adult islet beta cells, wherein an insulin content of the expanded and re-differentiated cells is at least 5% of total cellular protein following glucose stimulation.

According to yet another aspect of the present invention there is provided a method of ex-vivo expanding adult islet beta cells comprising incubating adult islet beta cells in a medium comprising CMRL-1066, thereby ex-vivo expanding the adult islet beta cells.

According to still another aspect of the present invention there is provided a method of ex-vivo expanding and re-differentiating adult islet beta cells comprising incubating adult islet beta cells in a medium comprising CMRL-1066, thereby obtaining expanded adult islet beta cells and providing the expanded adult islet beta cells with at least one beta cell differentiation promoting agent, thereby expanding and re-differentiating adult islet beta cells.

According to an additional aspect of the present invention there is provided a method of ex-vivo increasing insulin content in adult islet beta cells comprising providing a quantity of betacellulin sufficient to increase insulin content in the adult islet beta cells.

According to yet an additional aspect of the present invention there is provided a method of treating diabetes in a subject, comprising transplanting a therapeutically effective amount of a population of ex-vivo expanded and re-differentiated adult islet beta cells, whose insulin content is at least 5% of total cellular protein following glucose stimulation, into the subject, thereby treating diabetes.

According to still an additional aspect of the present invention there is provided a use of the population of ex-vivo expanded and re-differentiated adult islet beta cells, whose insulin content is at least 5% of total cellular protein following glucose stimulation, to treat diabetes in a subject.

According to a further aspect of the present invention there is provided a medium for expanding adult islet beta cells comprising medical grade CMRL-1066.

According to yet a further aspect of the present invention there is provided a pharmaceutical composition comprising as an active ingredient the population of ex-vivo expanded and re-differentiated adult islet beta cells whose insulin content is at least 5% of total cellular protein following glucose stimulation, and a pharmaceutically acceptable carrier.

According to further features in preferred embodiments of the invention described below, the adult islet beta cells are trypsinized According to still further features in the described preferred embodiments the method of ex-vivo increasing insulin content in adult islet beta cells further comprises providing the adult islet beta cells at least one beta cell differentiation promoting agent.

According to still further features in the described preferred embodiments the islet markers comprise beta cell markers.

According to still further features in the described preferred embodiments the beta cell markers comprise PC1/3 and PC2.

According to still further features in the described preferred embodiments the islet markers are selected from the group consisting of Isl-1, somatostatin and pancreatic polypeptide.

According to still further features in the described preferred embodiments the ex-vivo expanded adult islet beta cells are characterized by a replication rate of seven days.

According to still further features in the described preferred embodiments the ex-vivo expanded and re-differentiated adult islet beta cells are glucose responsive.

According to still further features in the described preferred embodiments the medium comprises serum.

According to still further features in the described preferred embodiments the serum comprises fetal calf serum or fetal bovine serum.

According to still further features in the described preferred embodiments the medium further comprises glucose.

According to still further features in the described preferred embodiments a concentration of glucose is 5.6 mM.

According to still further features in the described preferred embodiments the medium comprises antibiotics.

According to still further features in the described preferred embodiments providing the adult islet beta cells at least one beta cell differentiation promoting agent comprises expressing in the adult islet beta cells the at least one at least one beta cell differentiation promoting agent.

According to still further features in the described preferred embodiments providing the adult beta cells at least one beta cell differentiation promoting agent comprises incubating the adult islet beta cells in a medium comprising the at least one beta cell differentiation promoting agent.

According to still further features in the described preferred embodiments providing the adult islet beta cells an amount of betacellulin sufficient to increase insulin content comprises expressing in the adult islet beta cells betacellulin.

According to still further features in the described preferred embodiments providing the adult islet beta cells an amount of betacellulin sufficient to increase insulin content comprises incubating the adult islet beta cells in a medium comprising betacellulin.

According to still further features in the described preferred embodiments the quantity of betacellulin sufficient to increase insulin content is selected from a range between 0.5 and 8 nM.

According to still further features in the described preferred embodiments the medium is CMRL-1066.

According to still further features in the described preferred embodiments medium further comprises glucose.

According to still further features in the described preferred embodiments the medium further comprises antibiotics.

According to still further features in the described preferred embodiments the population of ex-vivo expanded and re-differentiated adult islet beta cells is genetically modified to express a pharmaceutical agent.

According to still further features in the described preferred embodiments the pharmaceutical agent reduces immune mediated rejection.

According to still further features in the described preferred embodiments the insulin content is equivalent to the insulin content in normal adult islet beta cells.

According to still further features in the described preferred embodiments the at least one beta cell differentiation promoting agent is a transcription factor.

According to still further features in the described preferred embodiments the transcription factor is selected from the group consisting of NeuroD, Ngn3, Pax6, Pax4, NRx2.2, NRx6.1, Pdx-1 and Isl-1.

According to still further features in the described preferred embodiments the transcription factor is Ngn3.

According to still further features in the described preferred embodiments the at least one beta cell differentiation promoting agent is betacellulin.

The present invention successfully addresses the shortcomings of the presently known configurations by providing conditions for expanding adult human islet cells, as well as methods for their redifferentiation. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 8:
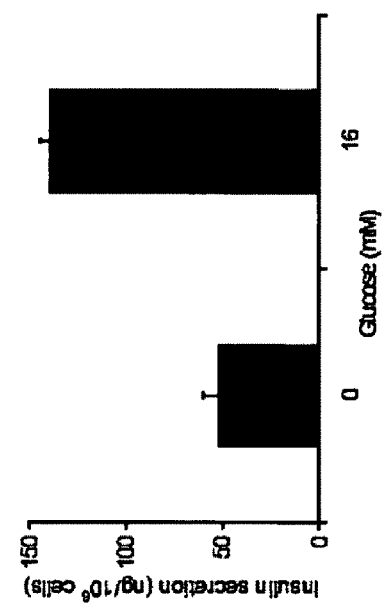

FIGS. 1A-H are confocal fluorescent microscope images of cells which have been incubated for the indicated number of days during the first two weeks in "expansion medium". All nuclei are stained blue with DAPI. Bar=50 μm, except for D, in which bar=20 μm. FIG. 1A is a phase contrast image of intact islets. FIG. 1B is a phase contrast image of an islet cell monolayer. FIG. 1C is a phase contrast image of an islet cell monolayer following three days in expansion medium highlighting antibody labeled insulin and ki67. FIG. 1D is a phase contrast image of an islet cell monolayer following seven days in expansion medium highlighting antibody labeled insulin and ki67. FIG. 1E is a phase contrast image of an islet cell monolayer following ten days in expansion medium highlighting antibody labeled PC1/3 and BrdU. FIG. 1F is a phase contrast image of an islet cell monolayer following ten days in expansion medium highlighting antibody labeled PC2 and BrdU. FIG. 1G is a phase contrast image of COS1 cells in expansion medium highlighting antibody labeled PC1/3. FIG. 1H is a phase contrast image of COS1 cells in expansion medium highlighting antibody labeled PC2.

FIGS. 2A-B are light (FIG. 2A) and fluorescent (FIG. 2B) microscope images of proliferating human islet-derived (PHID) cells following one week in culture. FIG. 2A depicts staining for BrdU incorporation. FIG. 2B depicts double-labeling with BrdU (red) and insulin (green) antibodies at a higher magnification.

FIGS. 3A-B are photographs depicting dedifferentiation of PHID cells as demonstrated by RT-PCR analyses following the indicated number of passages in culture. Transcripts were analyzed with the indicated primers, in comparison with a negative control (−, minus-template) and a positive control (+, human islet RNA). The GAPDH gene was used to monitor mRNA and cDNA quality and loading.

FIGS. 4A-F are confocal fluorescent microscope images depicting immunostaining of PHID cells following five passages (FIGS. 4A-C) and seven passages (FIGS. 4D-F) in culture. FIG. 4A is a phase contrast image of PHID cells highlighting antibody labeled PC1/3(red) superimposed on DAPI staining (blue). FIG. 4B is a phase contrast image of PHID cells highlighting antibody labeled PC2 (red) superimposed on DAPI staining (blue). FIG. 4C is a phase contrast image of PHID cells highlighting antibody labeled PP (red) superimposed on DAPI staining (blue). FIG. 4D is a phase contrast image of PHID cells highlighting antibody labeled PP (red) superimposed on DAPI staining (blue). FIG. 4E is a phase contrast image of PHID cells highlighting antibody labeled PC1/3(red). FIG. 4F is a phase contrast image of the identical PHID cells shown in FIG. 4E stained with DAPI. Bar=50 μm.

FIGS. 5A-F are light (FIGS. 5A, 5C and 5E) and fluorescent (FIGS. 5B, 5D and 5F) microscope images illustrating the reduction of GFP fluorescence in cultured mouse MIP-GFP islets.

FIGS. 6A-D are photographs and bar chart illustrating the effect of betacellulin (BTC) on redifferentiation of PHID cells. FIG. 6A is a photograph of RT-PCR analysis of PHID cells (passage 5) treated for six days with exendin-4 (lane 1), BTC (lane 2), activin A (lane 3), serum-free medium (lane 4), and expansion medium (lane 5). FIG. 5B is a photograph of RT-PCR analysis of PHID cells (passage 5) treated for six days with BTC. FIG. 5C is a photograph of RT-PCR analysis of PHID cells (passage 6) treated for six days with BTC at the indicated concentrations in serum-free medium (except for the lane marked with asteric, in which complete medium with serum was used). Transcripts were analyzed with the indicated primers, in comparison with a negative control (−, minus template) and a positive control (+, human islet RNA). In FIG. 6B, the amount of human islet RNA was 5× lower, compared with PHID cell RNA. FIG. 6D is a bar graph indicating insulin content in passage 6 PHID cells treated for 6 days with the indicated concentration of betacellulin in complete medium. Values are mean±SD (n=3).

FIGS. 7A-G are fluorescent microscope images depicting the effect of BTC on insulin expression in PHID cells. FIG. 7A is an immunofluorescence analysis image of cells from donor #7 (passage 5) in the absence of BTC photographed at a high exposure for Cy3, to visualize weak insulin staining. FIG. 7B is an immunofluorescence analysis image of cells from donor #7 (passage 5) following BTC treatment photographed at a high exposure for Cy3, to visualize weak insulin staining. FIG. 7C is an immunofluorescence analysis image of cells from donor #7 (passage 5) in the absence of BTC photographed at a low exposure for Cy3, to visualize fields with intensely-stained cells. FIG. 7D is an immunofluorescence analysis image of cells from donor #7 (passage 5) following BTC treatment photographed at a low exposure for Cy3, to visualize fields with intensely-stained cells. For FIGS. 7A-D, bar=50 μm. FIGS. 7E and 7F are immunofluorescence analysis images of cells from passage 5 in the absence of betacellulin treatment. FIG. 7E depicts insulin staining alone and FIG. 7F depicts DAPI staining alone. FIG. 7G is an immunofluorescence analysis image of cells from passage 5 following betacellulin treatment in serum-free medium depicting double staining for DAPI and insulin.

FIG. 8 is a bar graph illustrating the effect of BTC on glucose induced insulin secretion in PHID cells at passage 5. Values are mean±SD (n=3).

FIGS. 9A-D are photographs and construct illustrations depicting the effect of Ngn3 on redifferentiation of PHID cells (passage 5). FIG. 9A is an illustration of the tet-Ngn3 construct. The Ngn3 cDNA was placed under control of a minimal promoter and the tet-operator sequences (tet-op) and upstream of an IRES (internal ribosome entry site) element of the pIRES vector, which also includes a neomycin resistance gene (Neo) and a woodchuck hepatitis virus posttranscriptional modification element (WHV). FIG. 9B is an illustration of the CMV-rtTA construct—PcDNA6/TR (Invitrogen) containing the blasticidin resistance gene under the control of the SV40 promoter ($SV40_p$) and the reverse tetracycline transactivator (rtTA) under the control of the CMB promoter ($CMV_p$). FIG. 9C is a photograph of RT-PCR analysis following the stable transfection of the inducible tet-on NGN3 gene and incubation for 3 weeks in the absence or presence of doxycycline (dox). FIG. 9D is a photograph of immunofluorescence analysis with an insulin antibody following the stable transfection of the inducible tet-on NGN3 gene and incubation for 3 weeks in the absence or presence of doxycycline (dox). They were then analyzed for gene expression by RT-PCR and immunofluorescence.

DESCRIPTION OF THE PREFERRED EMBODIMENTS

The present invention is of an expanded and re-differentiated population of adult beta cells capable of both storing insulin in physiological amounts and secreting insulin in response to glucose. The present invention can be used in cell replacement therapy in the treatment of insulin dependant diabetes.

The principles and operation of the expanded and re-differentiated isolated population of adult beta cells according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Type I diabetes is caused by the autoimmune destruction of the pancreatic islet insulin-producing beta cells. Insulin administration does not prevent the long-term complications of the disease, since the optimal insulin dosage is difficult to adjust. Replacement of the damaged cells with regulated insulin-producing cells is considered the ultimate cure for type 1 diabetes. Pancreas transplantation has been successful but is severely limited by the shortage of donors. With the development of new islet isolation and immunosuppression procedures, significant success has been reported using islets from 2-3 donors per recipient (Shapiro A M, Lakey J R, Ryan E A et al. New Engl J Med 2000; 343:230-238). This progress underscores the urgent need for developing alternatives to human pancreas donors, namely abundant sources of cultured human β cells for transplantation.

While reducing the present invention to practice, the present inventors have uncovered a novel approach for ex-vivo expansion of isolated adult islet beta cells while still maintaining islet marker expression. The present inventors have also uncovered novel conditions for increasing insulin content in cells (i.e., re-differentiating cells) propagated according to the teachings of the present invention. The present invention exploits these finding to provide a viable source of functioning beta cells for transplantation into diabetic patients.

As is illustrated hereinbelow and in the Examples section which follows the present inventor has uncovered that isolated adult islet beta cells may be propagated in CMRL-1066 for at least sixteen passages, without a noticeable change in cell replication rate and without detectable apoptosis representing an expansion of over 65,000-fold. During propagation, the isolated beta cells undergo de-differentiation (although not complete, as the expanded cells still express a set of islet markers). Dedifferentiation may be measured by a decrease in transcription of key genes expressed in normal, quiescent beta cells, as illustrated in FIGS. 4A-F. The present inventor has also uncovered that the expanded cell population of the present invention may be re-differentiated by addition of betacellulin and/or Ngn-3. As illustrated in Example 2, the re-differentiated cells are capable of storing physiological concentrations of insulin and secreting therapeutic quantities of insulin in response to glucose.

The present invention overcomes prior art limitations in various aspects. Ex-vivo adult and fetal human islet cells cultured according to prior art teachings have been shown to proliferate at the most for 10-15 population doublings, after which they undergo senescence (Halvorsen T L, et al., J Endocrinol 2000; 166:103-109). The expanded adult islet beta cells of the present invention are propagatable for at least sixteen passages.

Both committed and non-committed cells have been shown to differentiate into insulin producing cells. In sharp contrast to the present invention, these cells are not capable of secreting therapeutic concentrations of insulin in response to glucose.

U.S. Pat. Appl. No. 20040132679 teaches administration of betacellulin in conjunction with islet cell differentiation transcription factors for the treatment of type I Diabetes. In sharp contrast to the present invention, U.S. Pat. Appl. No. 20040132679 does not teach differentiation of an expanded population of adult islet beta cells. Furthermore, when administered alone, betacellulin had no effect on the serum glucose of STZ induced diabetic mice, indicating that betacellulin alone was not able to fully differentiate the hepatic cells.

Thus, according to one aspect of the present invention there is provided a method of ex-vivo expanding adult islet beta cells comprising incubating isolated adult islet beta cells in a medium comprising CMRL-1066, thereby ex-vivo expanding the adult islet beta cells.

As used herein the phrase "ex-vivo" refers to cells which are removed from a living organism and cultured outside the organism (e.g., in a test tube).

As used herein, the phrase "adult islet beta cells" refers to post-natal (e.g., non-embryonic) pancreatic islet endocrine cells which are capable of secreting insulin in response to elevated glucose concentrations and express typical beta cell markers. Examples of beta cell markers include, but are not limited to, insulin, pdx, Hnf3β, PC1/3, Beta2, NRx2.2, GLUT2 and PC2.

The isolated adult islet beta cells of this aspect of the present invention may be of homogeneous or heterogeneous nature.

Thus, for example, the adult islet beta cells of this aspect of the present invention may be comprised in isolated pancreatic islets. Islet cells may be comprised of the following: 1) beta cells that produce insulin; 2) alpha cells that produce glucagon; 3) delta cells (or D cells) that produce somatostatin; and/or F cells that produce pancreatic polypeptide. The polypeptide hormones (insulin, glucagon, somatostatin and pancreatic polypeptide) inside these cells are stored in secretary vesicles in the form of secretory granules.

Methods of isolating islets are well known in the art. For example, islets may be isolated from pancreatic tissue using collagenase and ficoll gradients. An exemplary method is described in Example 1 herein below.

Preferably the adult islet beta cells of the present invention are dispersed into a single cell suspension—e.g. by the addition of trypsin or by trituration.

The adult islet beta cells may be further isolated being substantially free from other substances (e.g., other cells, proteins, nucleic acids, etc.) that are present in its in-vivo environment e.g. by FACs sorting.

The adult islet beta cells may be obtained from any autologous or non-autologous (i.e., allogeneic or xenogeneic) mammalian donor. For example, cells may be isolated from a human cadaver.

As used herein, the term "expanding" refers to increasing the number and overall mass of adult islet beta cells of the present invention by the process of cell division, rather than simply enlarging by hypertrophy. As described in Example 1 herein below, adult islet beta cells may be expanded by passaging the cells every seven days and refeeding twice a week. According to the teachings of the present invention the adult islet beta cells may be expanded 65,000 fold without any detectable apoptosis.

As used herein, the term "CMRL 1066" refers to the serum free medium, originally developed by Connaught Medical Research Laboratories for the culture of L cells, and includes any other derivations thereof provided that the basic function of CMRL is preserved. CMRL-1060 medium is commercially available in either liquid or powder form from companies including Gibco BRL, Grand Island, N.Y., catalogue number 11530-037; Cell and Molecular Technologies, Phillipsburg N.J.; Biofluids Inc, Rockville, Md.; Bioreclamation Inc. East Meadow, N.Y.; United States Biological, Swampscott, Mass.; Sigma Chemical Company, St. Louis, Mo.; Cellgro/Mediatech, Herndon, Va. and Life technologies, Rockville Md.

Preferably the CMRL is of medical grade purity. Thus, there is provided a medium for expanding adult islet beta cells of medical grade purity. As used herein the phrase "medical grade purity" refers to both the constituents of CMRL and the final product being of medical grade purity (i.e., safe for administration). The CMRL medium of the present invention may further comprise supplementary constituents which may improve growth and/or viability of the adult islet beta cells. These include, but are not limited to, growth factors (e.g. hepatocyte growth factor, nerve growth factor and/or epidermal growth factor) serum (e.g. fetal calf serum or fetal bovine serum), glucose (e.g. 5.6 mM) and antibiotics. Exemplary antibiotics and their concentrations are described in the Examples section herein below.

Preferably, the adult islet beta cells are propagated as anchorage-dependent cells by attaching to a solid substrate (i.e., a monolayer type of cell growth). According to a preferred embodiment the adult islet beta cells may be in CMRL 1066 medium at 37° C. with 5% $CO_2$.

The adult islet beta cells generated according to the above teachings are propagatable ex-vivo for at least sixteen passages while demonstrating continuous expression of islet markers.

According to this aspect of the present invention, the term "continuous expression of islet markers" refers to a detectable mRNA/protein expression of islet markers throughout each round of cell division. Methods of detecting mRNA/protein expression are well known in the art and include but are not limited to Northern, RT-PCR, oligonucleotide microarray, Western, RIA, Elisa, FACS and immunohistochemical analysis.

The phrase "islet markers" refers to at least one mRNA and/or protein which is specifically expressed in the pancreatic islet. Preferably, at least one of the islet markers is a beta cell marker. As shown in the Examples section which follows, the adult islet beta cells expanded according to the teachings of the present invention were shown to express two beta cell markers PC1/3 and PC2. In addition, the expanded adult islet beta cells expressed somatostatin, pancreatic polypeptide and Isl-1.

The expanded adult islet beta cells of this aspect of the present invention do not express all typical beta cell markers. Thus as illustrated in FIGS. 3A-B, following expansion the adult islet beta cells do not express insulin, pd-x, neuro D and NRx2.2 and may be referred to as being in a state of de-differentiation.

As mentioned hereinabove, while further reducing the present invention to practice, the present inventor uncovered, a method of re-differentiating the expanded adult islet beta cells of the present invention. The method is effected by providing at least one beta cell differentiation promoting agent.

As used herein the term "re-differentiating" refers to the altering of a cell such that it passes from one of a less defined function to one of a more defined function (may also be referred to as more differentiated). For example, the defined functions of an adult beta cell include storing insulin and secreting insulin in response to glucose. Re-differentiation of the expanded adult islet beta cells of the present invention may include such processes as increasing beta cell insulin content, increasing sensitivity to glucose and/or increasing secretory apparatus. Methods of increasing beta cell insulin content may include increasing insulin transcription and/or post transcriptional control and/or increasing translation and/or post-translational control. Methods of increasing beta cell insulin content may also include enhancing insulin storage and/or retarding insulin breakdown. Methods of increasing sensitivity to glucose may include increasing the expression of glucose transporters.

As used herein a "beta cell differentiation promoting agent" refers to a molecule (e.g., a proteinaceous or nucleic molecule) which is able either alone or in combination with other beta cell differentiation promoting agents to re-differentiate expanded adult islet beta cells of the present invention using any of the mechanisms mentioned hereinabove.

Examples of beta cell differentiation promoting agents include but are not limited to Activin A, Atrial Natriuretic Peptide, Betacellulin, Bone Morphogenic Protein (BMP-2), Bone Morphogenic Protein (BMP-4), C natriuretic peptide (CNP), Caerulein, Calcitonin Gene Related Peptide (CGRP-ax), Cholecystokinin (CCK8-amide), Cholecystokinin octapeptide (CCK8-sulfated), Cholera Toxin B Subunit, Corticosterone (Reichstein's substance H), Dexamethasone, DIF-1, Differanisole A, Dimethylsulfoxide (DMSO), EGF, Endothelin 1, Exendin 4, FGF acidic, FGF2, FGF7, FGFb, Gastrin I, Gastrin Releasing Peptide (GRP), Glucagon-Like Peptide 1 (GLP-1), Glucose, Growth Hormone, Hepatocyte Growth Factor (HGF), IGF-1, IGF-2, Insulin, KGF, Lactogen, Laminin, Leu-Enkephalin, Leukemia Inhibitory Factor (LIF), Met-Enkephalin, n Butyric Acid, Nerve Growth Factor (.beta.-NGF), Nicotinamide, n-n-dimethylformamide (DMF), Parathyroid Hormone Related Peptide (Pth II RP), PDGF AA+PDGF BB MIX, PlGF (Placental GF), Progesterone, Prolactin, Putrescine Dihydrochloride Gamma-Irradiated Cell Culture, REG1, Retinoic Acid, Selenium, Selenious Acid, Sonic Hedgehog, Soybean Trypsin Inhibitor, Substance P, Superoxide Dismutase (SOD), TGF-.alpha., TGF-.beta. sRII, TGF-.beta.1, transferrin, Triiodothyronine (T3), Trolox, Vasoactive Intestinal Peptide (VIP), VEGF, Vitamin A and Vitamin E.

A beta cell differentiation promoting agent may also be a transcription factor. The term "beta cell differentiation transcription factor" as used herein is defined as any molecule, either a polypeptide or a nucleic acid expressing the polypeptide, which is involved in beta cell differentiation by functioning as a transcription factor. The transcription factor may also participate in additional mechanisms directed to development, metabolism or the like. Examples of beta cell differentiation transcription factor include, but are not limited to, NeuroD (GenBank Accession No. AAA93480), Pax6 (GenBank Accession No. AAK95849), Pax4 (GenBank Accession No. AAD02289), NRx2.2 (GenBank Accession No. AAC83132), NRx6.1 (GenBank Accession No. AAD11962), Isl-1 (GenBank Accession No. NP002193), Pd-x (GenBank Accession No. AAA88820) or Ngn3 (GenBank Accession No. AAK15022) and homologues or orthologues of same.

According to a preferred embodiment of this aspect of the present invention the beta cell differentiation promoting agent is betacellulin (GenBank Accession No. XP172810) or a functional portion thereof e.g. EGF binding domain [Riese D. J. et al., Oncogene. 1996 Jan. 18; 12(2):345-53]. The term may be used to encompass any polypeptide which comprises betacellulin activity i.e. functions as a ligand for an EGF (epidermal growth factor) receptor protein, and participates in the growth and differentiation mechanisms of islet cells in a pancreas. Determination of betacellulin functional portions which may be used in accordance with the present invention may be achieved using assays familiar to those of skill in the art. In one embodiment, the betacellulin polypeptide is a full-length protein, i.e., preprotein or betacellulin precursor, that has not been proteolytically cleaved such as in amino acid sequences as set forth in AAA40511, Q05928 and P35070. Examples of betacellulin homolog gene sequences include GenBank Accession Nos. AAA40511; NP071592; AAM21214; XP124577; NPO31594; NP001720; BAA96731; AAF15401; AAB25452; AAA40511.

The beta cell differentiation promoting agents of the present invention may be synthesized using any technique known to those of skill in the art, including the expression of proteins, polypeptides or peptides through standard molecular biological techniques, the isolation of polypeptides from natural sources, or the chemical synthesis of polypeptides.

For example beta cell differentiation promoting agents may be synthesized using solid phase peptide synthesis procedures that are well known in the art and further described by John Morrow Stewart and Janis Dillaha Young, [Solid Phase Peptide Syntheses (2nd Ed., Pierce Chemical Company, 1984)]. Synthetic peptides can be purified by preparative high performance liquid chromatography [Creighton T. (1983) Proteins, structures and molecular principles. WH Freeman and Co. N.Y.] and the composition of which can be confirmed by amino acid sequencing.

In cases where large amounts of the peptide are desired, they can be generated using recombinant techniques such as described by Bitter et al., (1987) Methods in Enzymol. 153: 516-544, Studier et al., (1990) Methods in Enzymol. 185:60-89, Brisson et al., (1984) Nature 310:511-514, Takamatsu et al., (1987) EMBO J. 6:307-311, Coruzzi et al., (1984) EMBO J. 3:1671-1680 and Brogli et al., (1984) Science 224:838-843, Gurley et al., (1986) Mol. Cell. Biol. 6:559-565 and Weissbach & Weissbach, 1988, Methods for Plant Molecular Biology, Academic Press, NY, Section VIII, pp 421-463.

The beta cell differentiation promoting agents may be synthesized as fusion proteins. These proteins are typically linked at the N- or C-terminus, to all or a portion of a second polypeptide. In the present invention, a fusion protein may comprise a beta cell differentiation transcription factor sequence and/or a betacellulin sequence together with a linking moiety or a reporter (detectable) molecule. The fusion may aid in stabilizing or assisting in the folding of the beta cell differentiation promoting agent. In other examples, the fusion protein employs leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

Alternatively, various commercial preparations of proteins, polypeptides and peptides are known to those of skill in the art. For example, betacellulin is commercially available from BTC; R&D Systems, Minneapolis, Minn.

The beta cell differentiation promoting agents of the present invention may be purified—e.g. by fractionation Following purification, beta cell promoting agents are typically assayed (e.g. by protein assays) to determine whether the purified protein has retained its activity.

Polypeptide agents for promoting beta cell differentiation may be provided to the adult islet beta cells per se. Alternatively, polynucleotides encoding same may be administered to the adult islet beta cells. In this case, the polynucleotide agent is ligated in a nucleic acid construct under the control of a cis-acting regulatory element (e.g. promoter) capable of directing an expression of the beta cell differentiation promoting agent in the adult islet beta cells in a constitutive or inducible manner.

The nucleic acid construct may be introduced into the expanded cells of the present invention using an appropriate gene delivery vehicle/method (transfection, transduction, etc.) and an appropriate expression system. Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Lipid-based systems may be used for the delivery of these constructs into the expanded adult islet beta cells of the present invention. Useful lipids for lipid-mediated transfer of the gene are, for example, DOTMA, DOPE, and DC-Chol [Tonkinson et al., Cancer Investigation, 14(1): 54-65 (1996)] Recently, it has been shown that Chitosan can be used to deliver nucleic acids to the intestine cells (Chen J. (2004) World J Gastroenterol 10(1):112-116). Other non-lipid based vectors that can be used according to this aspect of the present invention include but are not limited to polylysine and dendrimers.

The expression construct may also be a virus. Examples of viral constructs include but are not limited to adenoviral vectors, retroviral vectors, vaccinia viral vectors, adeno-associated viral vectors, polyoma viral vectors, alphaviral vectors, rhabdoviral vectors, lenti viral vectors and herpesviral vectors.

A viral construct such as a retroviral construct includes at least one transcriptional promoter/enhancer or locus-defining element(s), or other elements that control gene expression by other means such as alternate splicing, nuclear RNA export, or post-transcriptional modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably, the signal sequence for this purpose is a mammalian signal sequence or the signal sequence of the peptide variants of the present invention. Optionally, the construct may also include a signal that directs polyadenylation, as well as one or more restriction site and a translation termination sequence. By way of example, such constructs will typically include a 5' LTR, a tRNA binding site, a packaging signal, an origin of second-strand DNA synthesis, and a 3' LTR or a portion thereof.

Preferably the viral dose for infection is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles.

It will be appreciated that expression of more than one beta cell differentiation promoting agent in the expanded cells of the present invention may be desired. Various construct schemes can be utilized to express more than one beta cell differentiation promoting agent from a single nucleic acid construct.

For example, the two recombinant proteins can be co-transcribed as a polycistronic message from a single promoter sequence of the nucleic acid construct.

To enable co-translation of both beta cell differentiation promoting agents from a single polycistronic message, the first and second polynucleotide segments can be transcriptionally fused via a linker sequence including an internal ribosome entry site (IRES) sequence which enables the translation of the polynucleotide segment downstream of the IRES sequence. In this case, a transcribed polycistronic RNA molecule including the coding sequences of both the first and the second growth factors will be translated from both the capped 5' end and the internal IRES sequence of the polycistronic RNA molecule to thereby produce both beta cell differentiation promoting agents.

Alternatively, the first and second polynucleotide segments can be translationally fused via a protease recognition site cleavable by a protease expressed by the cell to be transformed with the nucleic acid construct. In this case, a chimeric polypeptide translated will be cleaved by the cell expressed protease to thereby generate both beta cell differentiation promoting agents.

Still alternatively, the nucleic acid construct of the present invention can include two promoter sequences each being for separately expressing both beta cell differentiation promoting agents. These two promoters which may be identical or distinct can be constitutive, tissue specific or regulatable (e.g. inducible) promoters functional in one or more cell types.

The beta cell differentiation promoting agents, either alone or in combination, may be provided to ex-vivo cultured adult islet beta cells by addition to the incubating medium. According to one embodiment betacellulin is provided alone in a quantity that is sufficient to increase insulin content in the adult islet beta cells. The phrase "insulin content" refers to the amount of mature insulin inside an adult beta cell. Measurement of insulin content is well known in the art. An exemplary method is extraction of cellular insulin with 3 M acetic acid as described in the Examples section which follows. The amount of mature insulin extracted from the adult islet beta cells may be determined using an ELISA kit commercially available from Mercodia, Uppsala, Sweden.

Typically, the concentration range of betacellulin that is sufficient to increase insulin content is between 0.5 and 8 nM. Preferably, the ex-vivo cultured adult islet beta cells are differentiated with betacellulin for at least six days.

Any medium may be used to incubate the expanded adult islet beta cells in the presence of the beta cell differentiation promoting agent. According to one embodiment, the medium is CMRL-1066. The medium may also comprise other agents such as glucose, serum and antibiotics.

Following the ex-vivo re-differentiation of the expanded adult islet beta cells of the present invention a population of adult islet beta cells are generated whose insulin content is at least 5% of total cellular protein following glucose stimulation.

As used herein the phrase "glucose stimulation" refers to the addition of glucose at a concentration of 16 mM for thirty minutes. This relieves the islet beta cells of a certain percent of their stored insulin.

Methods of determining total cellular protein are well known in the art (e.g. Bradford assay).

Methods of determining insulin content are provided herein above and in the Examples section which follows.

Preferably the amount of insulin in adult islet beta cell is greater than 5% of total cellular protein. Preferably the amount of insulin in adult islet beta cell is 10% of total cellular protein, even more preferably 15% and even more preferably 20%. Restoration of insulin content to 20% of total cellular protein represents a level in the range of that of normal beta cells. As used herein a "normal beta cell" refers to an in-vivo functioning beta cell. The amount of insulin in a normal beta cell may be calculated using the supposition that human pancreata comprise 1-15 grams of insulin, which contains about $10^9$ islet cells.

The redifferentiated adult islet beta cells of the present invention are glucose responsive. According to this aspect of the present invention, the phrase "glucose responsive" refers to the ability of the re-differentiated adult islet beta cells of the present invention to secrete insulin in response to glucose. Preferably, the adult islet beta cells secrete at least twice the quantity of insulin in response to 16 mM glucose as they secrete at 0 mM glucose.

The population of adult islet beta cells of the present invention may be further modified (e.g. genetic modification) to express a pharmaceutical agent such as a therapeutic agent, a telomerase gene, an agent that reduces immune mediated rejection or a marker gene. It is contemplated that therapeutic agents such as antimetabolites (e.g., purine analogs, pyrimidine analogs), enzyme inhibitors and peptidomimetics may be generally useful in the present invention. An example of a gene that may reduce immune mediated rejection is the uteroglobin gene. Uteroglobin is a protein expressed during pregnancy that confers immunologic tolerance and prevents inflammatory reactions. Methods of genetically modifying the adult islet beta cells of the present invention are described hereinabove.

Since the adult islet pancreatic cells of the present invention store and secrete insulin, they may be used for treating a disease which is associated with insulin deficiency such as diabetes.

Thus, according to another aspect of the present invention there is provided a method of treating diabetes in a subject, the method comprising transplanting a therapeutically effective amount of the population of ex-vivo expanded and re-differentiated adult islet beta cells of the present invention into the subject, thereby treating diabetes.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to providing the rediffentiated adult islet beta cells of the present invention, using any suitable route. Typically, beta cell therapy is effected by injection using a catheter into the portal vein of the liver, although other methods of administration are envisaged.

As mentioned hereinabove, the adult islet beta cells of the present invention can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylidene-acetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

The adult islet beta cells of the present invention may be transplanted to a human subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the adult islet beta cells of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (insulin producing cells) effective to prevent, alleviate or ameliorate symptoms of a disorder (e.g., diabetes) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. STZ diabetic mice) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat.

Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

The aim of the following experiments was to develop culture conditions which allow significant expansion of adult human islets from cadaver donors, as well as treatments to restore their differentiation following expansion.

Example 1

Replication and Dedifferentiation of Cultured Adult Human Islets

Materials and Methods

Islet isolation and expansion in tissue culture (human, mouse): Ficol-gradient purified adult human islets were obtained from Dr. Kevan Herold at the Columbia University Diabetes Center as described (Shapiro A M, et al., New Engl J Med 343:230-238, 2000). Briefly, islets were isolated from pancreata obtained from organ donors following a cold ischemia time of 6.1±2.9 hrs. The pancreatic duct was perfused with a cold enzyme mixture containing Liberase HI (Roche, Indianapolis, Ind.). Tissue was then transferred to a Ricordi chamber and separated by gentle mechanical agitation and enzymatic digestion at 37° C. Islets were purified with the use of discontinuous gradients of ficoll-diatrizoic acid (Lakey J R et al., Cell Transplant 8:285-292, 1999) in an aphaeresis system (model 2991, Cobe Laboratories, Lakewood, Colo.). The discontinuous ficoll gradient used solution densities of 1.108, 1.096, and 1.037 g/ml layered upon each other before the separation step. During centrifugation, islets migrated to the interfaces between 1.037 and 1.096 g/ml, and 1.096 and 1.108 g/ml (Lake S. P. et al., Diabetes 38 Suppl 1:143-145, 1989). The cellular material between these two interfaces was pooled and had a final purity of 71.5±26.2% and a viability of 85.2±6.7%. The stimulation index (insulin secreted in response to 16.7/1.67 mM glucose) was 3.27±1.78. Islets were maintained in CMRL 1066 medium at 37° C. with 5% $CO_2$ for 1-7 days before use.

Mouse islets were purified from mouse insulin promoter-green fluorescent protein (MIP-GFP) mice (Hara M. et al., Am J Physiol Endocrinol Metab 2003; 284:E177-E183) as described (Gotoh M. et al., Transplantation 1985; 40:437-438).

Islets were dissociated by incubation in trypsin at 37° C. for 5 minutes. Trypsinized cells were cultured in expansion medium consisting of CMRL 1066 medium containing 5.6 mM glucose and supplemented with 10% FCS, 100 U/ml penicillin, 100 μg/ml streptomycin, and 5 μg/ml amphotericine B. The cultures were refed twice a week and split 1:2 once a week.

Histological analyses Cells were plated in 24-well plates on sterilized coverslips and fixed in 4% paraformaldehyde. For Ki67 staining cells were permeabilized with 0.25% NP40 for 10 minutes. Cells were blocked for 10 min at room temperature in 1% bovine serum albumin, 10% FBS and 0.2% saponin, and incubated with the following primary antibodies diluted in blocking solution, overnight at 4° C.: mouse-anti-insulin 1:1000 (Sigma, St. Louis, Mich.); guinea pig-anti-insulin (1:200; Linco); rabbit-anti-Ki67 1:50 (ZYMED Laboratories Inc., South San Francisco, Calif.); rabbit-anti-PC1/3 1:500 or 1:200; rabbit-anti-PC2 1:1000 (both gifts from D. Steiner); and rabbit-anti-PP1:200 (DakoCytomation, Denmark) or rabbit-anti-PP (1:500; Linco). The bound antibody was visualized with a fluorescent secondary antibody: Cy3-goat-anti-mouse and -anti-rabbit 1:200 (Biomeda, Foster City, Calif.); rhodamine-goat-anti-guinea pig (1:200; Santa Cruz); and Alexa Fluor 488-goat-anti-rabbit 1:200 (Molecular Probes Europe BV, Leiden, The Netherlands), under a Zeiss confocal microscope. For double-immunofluorescence of insulin and BrdU, the primary anti-BrdU antibody was visualized with Texas red-goat-anti-mouse (1:200; Santa Cruz), and the primary anti-insulin antibody with Cy2-donkey-anti-guinea pig (1:400; Santa Cruz). Nucleii were visualized with 1 μg/ml DAPI (Roche) staining for 5 minutes at room temperature. BrdU staining was performed as previously described (Efrat S. et al., Proc Natl Acad Sci USA 1995; 92:3576-3580). Nuclear area was quantitated with ImageJ software (NIH, version 1.33u) by counting cells in >4 random fields.

RT-PCR: Total RNA was extracted from cultured cells and human pancreatic islets using High Pure RNA isolation kit (Roche Molecular Biochemicals, Mannhein, Germany). Specific transcripts were analyzed with SuperScript III RT-PCR kit (Invitrogen) according to the manufacturers' instructions. The absence of DNA contamination in RNA samples was confirmed with PCR primers flanking an intron. cDNA was amplified for 30-40 cycles (94° C. for 45 seconds; annealing under conditions indicated in Table 1 hereinbelow for 45 seconds; 72° C. for 40 seconds), using the primer pairs listed in Table 1 hereinbelow. PCR products were separated by electrophoresis in 1.5%-2.5 agarose gels and visualized by ethidium bromide staining.

Real-time cDNA quantitation was performed using Assays-on-Demand kits and an ABI Prism 7000 Sequence Detector (both from Applied Biosystems, Foster City, Calif.), according to the manufacturer's instructions. All reactions were performed in triplicate. The results were normalized to human large ribosomal protein PO cDNA.

TABLE 1

| Gene | cDNA size (bp) | Sense primer | Antisense primer | Annealing temp. |
|---|---|---|---|---|
| Insulin | 381 | GCTGCATCAGAAGAGGCATCAGG C (SEQ. ID. NO. 1) | GCGTCTAGTTGCAGTAGTTCTCCAG (SEQ. ID. NO. 2) | 58° C. |

TABLE 1-continued

| Gene | cDNA size (bp) | Sense primer | Antisense primer | Annealing temp. |
|---|---|---|---|---|
| GAPDH | 450 | ACCACAGTCCATGCCATCAC (SEQ. ID. NO. 3) | TCCACCACCCTGTTGCTGTA (SEQ. ID. NO. 4) | 58° C. |
| Chromogranin A | 543 | AAACGCTGGAGCAAGATGGAC (SEQ. ID. NO. 5) | GGGCAGGTAGGAGTCAGGAGTAG (SEQ. ID. NO. 6) | 61.8° C. |
| Glucagon | 437 | CGTTCCCTTCAAGACACAGAGGAG (SEQ. ID. NO. 7) | TCCCTGGCGGCAAGATTATC (SEQ. ID. NO. 8) | 56.8° C. |
| Glucokinase | 367 | TCACTGTGGGCGTGGATGG (SEQ. ID. NO. 9) | ACCGAAAAACTGAGGGAAGAGG (SEQ. ID. NO. 10) | 61.7° C. |
| Ngn3 | 406 | GCACGACCTCAACTCGGCAC (SEQ. ID. NO. 11) | CCTCTCCCTTACCCTTAGCACCC (SEQ. ID. NO. 12) | 62.5° C. |
| Beta2 NeuroD | 384 | AAGAACTACATCTGGGCTCTGTCG (SEQ. ID. NO. 13) | GCTGAGGGGTCCATCAAAGG (SEQ. ID. NO. 14) | 59.6° C. |
| IAPP | 350 | TTGAACCCAGGAGGCGGAG (SEQ. ID. NO. 15) | CTGCTGCTAACACACAATGAAACC (SEQ. ID. NO. 16) | 53.3° C. |
| NKX 2.2 | 369 | TCTGAACCTTGGGAGAGGGC (SEQ. ID. NO. 17) | GGTCATTTTGGCAACAATCACC (SEQ. ID. NO. 18) | 55° C. |
| Somatostatin | 169 | GACCCCAGACTCCGTCAGTTTC (SEQ. ID. NO. 19) | GCCTCATTTCATCCTGCTCAGC (SEQ. ID. NO. 20) | 57.8° C. |
| Glut-2 | 441 | CTTATGTGTTTTCCTCTTTGCTGG (SEQ. ID. NO. 21) | GAACCACCTGCCCTTTAGTGTAAC (SEQ. ID. NO. 22) | 52.4° C. |
| NKX 6.1 | 360 | ACACGAGACCCACTTTTTCCG (SEQ. ID. NO. 23) | TGCTGGACTTGTGCTTCTTCAAC (SEQ. ID. NO. 24) | 58.2° C. |
| ISL-1 | 504 | GGCAGTGAAGTAGCATCAATGTCC (SEQ. ID. NO. 25) | TGTTTGGCAAGGCAATGACC (SEQ. ID. NO. 26) | 52.6° C. |
| Kir6.2 | 451 | CCTTCCTTTTCTCCATTGAGGTCC (SEQ. ID. NO. 27) | AGGTCGTAGAGTGGGCTGTTGG (SEQ. ID. NO. 28) | 60.2° C. |
| PC1/3 | 404 | CTCCTAAAAGACTTGCGGAATCAC (SEQ. ID. NO. 29) | TCCACACAGGCACTAAGAAAGACTG (SEQ. ID. NO. 30) | 52.1° C. |
| PAX-6 | 395 | GCCAAATGGAGAAGAGAAGAAAAAC (SEQ. ID. NO. 31) | GTTGAAGTGGTGCCCGAGG (SEQ. ID. NO. 32) | 57.8° C. |
| Pdx1 | 277 | CTGCCTTTCCCATGGATGAA (SEQ. ID. NO. 33) | CGCTTCTTGTCCTCCTCCTTT (SEQ. ID. NO. 34) | 57.5° C. |
| Insulin | 280 | AACCAACACCTGTGCGGCTC (SEQ. ID. NO. 35) | GGGCTTTATTCCATCTCTCTCGG (SEQ. ID. NO. 36) | 61.1° C. |
| PC2 | 400 | GCATCAAGCACAGACCTACACTCG (SEQ. ID. NO. 37) | GAGACACAACCACCCTTCATCCTTC (SEQ. ID. NO. 38) | 60° C. |
| PP | 267 | CAATGCCACACCAGAGCAGATG (SEQ. ID. NO. 39) | TGGGAGCAGGGAGCAAGC (SEQ. ID. NO. 40) | 59° C. |

Results

Islet preparations devoid of detectable ductal sheets (FIG. 1A) were trypsinized and cultured in CMRL 1066 medium containing 5.6 mM glucose and supplemented with 10% FBS. Under these conditions the vast majority of cells adhered to the plate and formed a monolayer of cells with epithelial morphology. Cell size in the primary culture varied about 10-fold, as judged by measurement of nuclear area. Up to 60% of the islet cells were induced to replicate within the first 10 days of culture, as judged by BrdU incorporation as shown in Table 2 hereinbelow.

TABLE 2

| | | | | Nuclear area ($\mu m^2$) | | |
|---|---|---|---|---|---|---|
| Culture time | N | % Replicating | % Insulin$^+$ | All cells | Replicating | Insulin$^+$ |
| 3 d | 2481 | 11.4 | 15.4$^d$ | 89 ± 51$^{a,b}$ | 142 ± 59$^{a,b}$ | 57 ± 26$^c$ |
| 5 d | 1787 | 41.5 | 9.4$^d$ | 143 ± 67$^b$ | 175 ± 60$^{a,b}$ | 50 ± 35$^c$ |

TABLE 2-continued

| | | | | Nuclear area (μm²) | | |
| Culture time | N | % Replicating | % Insulin⁺ | All cells | Replicating | Insulin⁺ |
| --- | --- | --- | --- | --- | --- | --- |
| 10 d | 2732 | 59.5 | 5.6[d] | 139 ± 47[a] | 142 ± 52[b] | 35 ± 18[c] |
| 5 w | 1263 | 53.5 | 0.5[d] | 214 ± 97[a,b] | 171 ± 65 | n.d. |
| 5 w + 6 d BTC | 1954 | 25.1 | 10.9[d] | 199 ± 118 | 174 ± 105[b] | 43 ± 27[c] |

[a]p values compared with the immediate group below in the same column<4.5E−9
[b]p values compared with the group immediately to the right <1.3E−7
[c]p values compared with all cells on the same day <1.84E−33
[d]Intensely-stained cells Thus, following 3 days in culture, 11.4% of the cells were replicating. Two days later the percent of replicating cells increased to 41.5%, and by 10 days in culture (3 days after the first passage) the percentage rose to 59.5%. In sections of normal pancreas, about 80% of islet cells stain for insulin. However, in isolated human islets the percent of insulin⁺ cells is lower, reflecting a rapid dedifferentiation. In the dissociated islet culture, intense insulin staining was visible following 3-6 days in culture in 15.4% of the cells. Insulin staining was restricted to the smallest cells (nuclear area 57±26 μm²). Most of these cells were not labeled with two markers of proliferating cells, BrdU and Ki67. Nevertheless, occasional Ki67⁺ cells manifesting weak insulin staining could be observed (FIGS. 1C-D). Similarly BrdU⁺ cells manifesting weak insulin staining could be observed (FIGS. 2A-B), even though BrdU staining was seen in the majority of the larger (nuclear area 142±59 μm²), insulin-negative cells. After 5 days in culture the average cell size increased by 60% (nuclear area 143±67), and the percent of insulin⁺ cells decreased to 9.4%. After 10 days in culture the average cell size was unchanged and the percent of insulin⁺ cells was only 5.6%. Nevertheless, most of the replicating cells stained for the beta-cell markers, prohormone convertase (PC) 1/3 and PC2 (FIGS. 1E and 1F).

The doubling time of this cell population was 7 days. No significant cell mortality was observed, as judged by an apoptosis assay. These cells, termed PHID (proliferating human islet-derived) cells, were continuously propagated for 16 passages without a noticeable change in cell replication rate and without detectable apoptosis. This passage number represents an expansion of over 65,000-fold. The percent of proliferating cells remained stable following 5 weeks in culture, while the percent of insulin⁺-cells decreased to 0.5% (Table 2). The average nuclear area, compared with that of the 3 day-culture, increased by that time 2.4-fold (Table 2). After 4 months of continuous replication, significant cell senescence developed, as manifested by a greatly reduced replication rate, about once in 2 weeks. These results were reproducible with islets from multiple donors, both males and females, aged 27-73.

Cell replication was accompanied by a decrease in transcription of key genes expressed in normal, quiescent beta cells. Thus, Insulin mRNA levels decreased considerably by passage 3 and were barely detectable thereafter (FIGS. 3A and 3B). Similarly, expression of the β-cell transcription factors Pdx1, Beta2, and NRx2.2, as well as the glucose transporter GLUT2, was also down-regulated. In contrast, reduced levels of transcripts encoding the transcription factor Isl1, as well as PC1/3 and glucokinase (GK), persisted in the proliferating cells. Similarly to insulin, glucagon expression, as well as expression of the alpha-cell transcription factor Pax6, also decreased between passages 2-5. In contrast, expression of the genes encoding the islet hormones pancreatic polypeptide (PP) and somatostatin persisted until later passages. PC1/3 and PC2 immunostaining was detectable in the majority of cells at p. 5 (FIGS. 4A-C), indicating that the proliferating population was derived from beta cells and continued to express beta-cell markers. In addition, PP staining was observed in a large percent of the cells (FIG. 4C) suggesting the possibility of dedifferentiation to an islet precursor stage. These findings were confirmed by real-time RT-PCR quantitation as seen in Table 3 hereinbelow. RNA levels are expressed as a fraction of the RNA levels in freshly-isolated human islets. Values are mean±SD (n=3).

TABLE 3

| Gene | Relative expression |
| --- | --- |
| Insulin | 0.01 ± 0.01 |
| NKX2.2 | 0.002 ± 0.00 |
| GK | 0.13 ± 0.03 |
| PC1/3 | 0.11 ± 0.01 |
| PC2 | 0.13 ± 0.01 |

A similar dedifferentiation process was seen in cultured transgenic mouse islets expressing GFP under the insulin promoter (MIP-GFP), as judged by disappearance of the GFP fluorescence (FIGS. 5A-F).

Example 2

Restoration of Differentiation in PHID Cells

Materials and Methods

Cell treatment: PHID cells were incubated with the following factors for 6 days: activin A (Cytolab/PreproTech Asia, Rehovot, Israel; 10 nM), betacellulin (BTC; R&D Systems, Minneapolis, Minn., at the indicated concentrations), and exendin-4 (Sigma-Aldrich; 10 nM) in either serum-free or the expansion medium described above.

For incubation in serum-free medium, the cells were placed in CMRL 1066 medium containing antibiotics, in the presence of 10 μg/ml insulin, 5.5 μg/ml transferrin, and 5 ng/ml selenium (ITS, Sigma-Aldrich, Steinheim, Germany).

Insulin and human C-peptide secretion and cell content: Insulin secretion was measured by static incubation as previously described (Fleischer N, et al., Diabetes 47:1419-1425, 1998). Cells were plated in 24-well plates at 5×10⁴ cells per well. The cells were preincubated for 1 hour in Krebs-Ringer buffer (KRB), followed by incubation for 30 minutes in KRB containing 0.5 mM 1-isobutyl 3-methylxanthine (IBMX) and glucose at the indicated concentrations. The cells were then extracted in acetic acid, and the amount of insulin in the buffer and cell extract was determined using an ELISA kit (Mercodia, Uppsala, Sweden), which recognizes only mature insulin. Human C-peptide in the buffer and cell extract was determined using an ELISA kit (Mercodia, Uppsala, Sweden) according to the manufacturer's instructions.

Results

To induce re-differentiation, the dedifferentiated PHID cells were treated with a number of factors reported to affect beta-cell differentiation and proliferation. As seen in FIG. 6A, treatment with 4 nM betacellulin (BTC) resulted in restoration of expression of insulin mRNA, while exendin-4 had only a small effect at the concentration tested. In contrast, shift of the cells to serum-free medium for 6 days, or the use of activin A, did not restore insulin expression. The effect of BTC was further evaluated. To evaluate which concentration of BTC was the most effective, increasing concentrations of BTC were incubated with PHID cells and both beta-cell gene expression (FIG. 6C) insulin content was measured (FIG. 6D). Insulin ELISA assays revealed the restoration of the insulin content to 20% of total cellular protein with 1 nM of BTC, a level similar to that of normal a cells. A 6-day treatment with 1 nM BTC restored expression of multiple beta-cell genes, including insulin, transcription factors (Pdx1, NeuroD, NRx2.2, and NRx6.1), a gene involved in glucose sensing (GLUT2), and the beta-cell marker islet amyloid polypeptide (IAPP) (FIG. 6B). In addition, expression of Pax6 and glucagon was also increased. Intense insulin immunofluorescence was visible in 10.9% of cells following treatment with BTC, (a 22-fold increase) (FIG. 7C, and 7E-G Table 2). The intense insulin staining was restricted to the smallest cells (FIG. 7C, Table 2), which did not label with BrdU or Ki67. A similar percent of cells manifested intense staining for human C-peptide (FIG. 7D). In addition to the intense insulin staining, a weak staining for insulin was visible in many replicating cells following treatment with BTC (FIG. 7B). The percent of replicating cells decreased from 53.5% to 25.1% following BTC treatment (Table 2).

Consistent with re-appearance of insulin mRNA and immunostaining, insulin content increased in cells treated with BTC for six days as seen in Table 4 (PHID cells at passage 5) and Table 5 (PHID cells at passage 4-6) below.

TABLE 4

| Donor # | BTC (nM) | Insulin content (ng/$10^6$ cells) | Fold increase |
|---|---|---|---|
| 5 | 0 | 51 ± 1 | 1 |
|   | 0.5 | 10,687 ± 138 | 209 |
|   | 1 | 20,217 ± 495 | 396 |
|   | 1.5 | 16,226 ± 959 | 318 |
| 7 | 0 | 127 ± 71 | 1 |
|   | 0.5 | 1,613 ± 30 | 13 |
|   | 1 | 1,751 ± 195 | 14 |
|   | 2 | 1,952 ± 194 | 15 |
|   | 4 | 2,020 ± 240 | 16 |
|   | 6 | 2,382 ± 272 | 19 |
|   | 8 | 162 ± 59 | 1 |

TABLE 5

| | | | BTC Effect | | | |
|---|---|---|---|---|---|---|
| | | | Insulin Content (ng/$10^6$ cells) | | BTC Conc. | Fold | Serum |
| Donor # | Donor Sex | Donor Age | Untreated | Treated | (nM) | Stim. | Presence |
| 1 | m | 57 | 37 ± 30 | 66 ± 18 | 0.5 | 2 | + |
| 2 | m | 53 | 30 ± 7 | 575 ± 119 | 1 | 19 | − |
| 3 | f | 44 | n.d. | n.d. | 4 | n.d. | − |
| 4 | f | 73 | 129 ± 18 | 132 ± 9 | 1 | 0 | + |
| 5 | f | 51 | 51 ± 1 | 20,217 ± 495 | 1 | 396 | + |
| 6 | m | 49 | 133 ± 27 | 125 ± 6 | 1 | 0 | + |
| 7 | f | 54 | 127 ± 71 | 2,382 ± 272 | 6 | 19 | + |
| 8 | f | 27 | 126 ± 3 | 228 ± 8 | 4 | 2 | + |
| 9 | m | 58 | 110 ± 5 | 115 ± 9 | 4 | 0 | + |

The maximal increase in cellular insulin content in response to the indicated concentration of BTC is shown. Cells from donor #3 were analyzed only by RT-PCR.
n.d., ELISA not done.

A considerable difference was observed between the 9 donors tested with respect to the maximal insulin content restored (Table 5). Variability was also noted with respect to the most effective concentration of BTC. Thus, in donor #5, BTC at 1 nM induced a 396× increase in insulin content, while in donor #7 the maximal increase of 19× was obtained with 6 nM BTC. The restored insulin content in donor #5 represents 20% of total cellular protein, a level in the range of that of normal β cells. The insulin content in cells from donor #7 is consistent with the finding that only 10.9% of the cells manifested intense insulin immunostaining (FIGS. 7A-D and Table 2). Overall, BTC showed an inductive effect in 6 out of the 9 donors tested: in 4 of them it had a pronounced effect (including in one tested only at the RNA level—FIGS. 6A and B), while in 2 other donors it had only a 2-fold effect.

Insulin secretion from the redifferentiated cells was glucose-responsive, showing a 3-fold increase between 0 and 16 mM glucose; however, the basal level was high, compared with normal islets (FIG. 8). The percent of insulin content secreted at 16 mM glucose during a 30-minute period was 0.7%, which is similar to that of normal human islets. C-peptide secretion from these cells in response to 16 mM glucose was 82±21 ng/$10^6$ cells/30 minutes.

The dependence of the redifferentiated phenotype on the continuous presence of BTC was evaluated by switching the cells to regular growth medium lacking BTC. This resulted in a 38% decrease in insulin content following 7 days of culture.

Example 3

Restoration of Differentiation in PHID Cells by Expression of NGN3

Materials and Methods

Inducible expression of NGN3: The tet-Ngn3 plasmid was generated by placing the Ngn3 cDNA under control of a minimal promoter and tet-operator sequences (tet-op), and upstream of an IRES (internal ribosome entry site) element, a neomycin resistance gene (Neo), and a woodchuck hepatitis virus posttranscriptional modification element (WHV) as depicted in FIG. 9A. The tet-on transactivator plasmid PcDNA6/TR (Invitrogen) depicted in FIG. 9B was co-transfected with the tet-Ngn3 plasmid using Fugene6 liposome reagent (Roche) into de-differentiated PHID cells at passage 4 in expansion medium. Blasticydin selected was carried out at 2 µg/ml for 4 days. Induction of NGN3 expression was performed by incubation in 4 µg/ml doxycycline.

Results

The transfection efficiency of the tet-Ngn3 plasmid and PcDNA6/TR plasmid using this protocol was about 20%. Following blasticidine selection, cells were incubated±doxycycline (dox) to induce Ngn3 expression. As seen in FIG. 9C, in the absence of dox the levels of Ngn3 mRNA were bearly detectable. Induction with dox resulted in a great increase in Ngn3 expression. Inducible Ngn3 expression resulted in re-expression of insulin mRNA and protein (FIG. 9D), as well as β-cell genes involved in glucose sensing (GLUT2, glucokinase), the transcription factor NRx2.2, and the β-cell islet amyloid polypeptide (IAPP).

CONCLUSION

These data provide specific tissue culture conditions which can induce significant proliferation of adult human islet cells, as well as specific tissue culture conditions which can induce re-differentiation of the expanded cells. The variability amongst donors to BTC will require screening of a number of donors for finding a source of PHID cells, in which BTC can restore a sufficient insulin content to make them suitable for transplantation. Combined with appropriate means to prevent immune rejection, these methods will allow expansion of functional islet cells from single cadaveric donors for transplantation into multiple recipients.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A population of dedifferentiated adult islet cells generated by incubating isolated adult islet beta cells in a medium comprising CMRL-1066 and glucose, wherein a majority of said dedifferentiated adult islet cells express PC1/3 and do not express insulin.

2. The population of dedifferentiated adult islet cells of claim 1, expressing Isl-1.

* * * * *